(12) United States Patent
Zhu et al.

(10) Patent No.: US 7,282,505 B2
(45) Date of Patent: Oct. 16, 2007

(54) RAPAMYCIN POLYMORPHS AND USES THEREOF

(75) Inventors: Tianmin Zhu, Monroe, NY (US); Mahdi B. Fawzi, Morristown, NJ (US)

(73) Assignee: Wyeth, Madison, NJ (US)

( * ) Notice: Subject to any disclaimer, the term of this patent is extended or adjusted under 35 U.S.C. 154(b) by 152 days.

(21) Appl. No.: 11/206,472

(22) Filed: Aug. 18, 2005

(65) Prior Publication Data

US 2006/0040971 A1   Feb. 23, 2006

Related U.S. Application Data (60) Provisional application No. 60/603,096, filed on Aug. 20, 2004.

(51) Int. Cl.
*C07D 498/18* (2006.01)
*A61K 31/436* (2006.01)

(52) U.S. Cl. .................................. 514/291; 540/456

(58) Field of Classification Search ............... 540/456; 514/291
See application file for complete search history.

(56) References Cited

U.S. PATENT DOCUMENTS 3,929,992 A   12/1975  Sehgal et al.
3,993,749 A   11/1976  Sehgal et al.

FOREIGN PATENT DOCUMENTS

EP        0652219 A1      5/1995

OTHER PUBLICATIONS

Vézina et al., "Rapamycin (AY-22,989), A New Antifungal Antibiotic, I. Toxonomy of the Producing Streptomycete and Isolation of the Active Principle", J. Antibiot., 28, 721 (Oct. 1975).
Sehgal et al., "Rapamycin (AY-22,989), A New Antifungal Antibiotic, II. Fermentation, Isolation and Characterization", J. Antibiot. 28, 727 (Oct. 1975).
Baker et al., "Rapamycin (AY-22,989), A New Antifungal Antibiotic, III. In Vitro and In Vivo Evaluation", J. Antibiot. 31, 539 (Jun. 1978).
Swindells et al., "The X-ray Crystal Structure of Rapamycin, $C_{53}H_{79}NO_{13}$" Can. J. Chem., 56: 2491 (1978).

*Primary Examiner*—Bruck Kifle
(74) *Attorney, Agent, or Firm*—Arnold S. Milowsky; Howson & Howson LLP (57) ABSTRACT

The present invention provides rapamycin polymorph Form II. This invention also provides processes for preparing rapamycin polymorph Form II and pharmaceutical compositions including rapamycin polymorph Form II.

19 Claims, 2 Drawing Sheets

RAPAMYCIN POLYMORPHS AND USES THEREOF

CROSS-REFERENCE TO RELATED APPLICATIONS

This application claims the benefit under 35 USC 119(e) of U.S. Patent Application No. 60/603,096, filed Aug. 20, 2004.

BACKGROUND OF THE INVENTION

This invention relates to rapamycin polymorph Form II.

Rapamycin is a macrocyclic triene antibiotic produced by *Streptomyces hygroscopicus*, which was initially identified as having antifungal activity, particularly against *Candida albicans*, both in vitro and in vivo (C. Vezina et al., *J. Antibiot.* 28, 721 (1975); S. N. Sehgal et al, *J Antibiot.* 28, 727 (1975); H. A. Baker et al, *J Antibiot.* 31, 539 (1978); U.S. Pat. Nos. 3,929,992 and 3,993,749). Rapamycin is commercially available as Sirolimus (Wyeth).

Rapamycin is widely used as an immunosuppressant in organ transplant recipients and has shown limited toxicities even in combination schedules with other immunosuppressants like cyclosporine or corticosteroids. The intracellular rapamycin receptor is a small protein termed FKBP12 (FK506-binding protein). The FKBP-rapamycin complex inhibits the function of a serine/threonine kinase, mTOR (mammalian target of rapamycin), thereby blocking stimulation of the ribosomal s6 kinase p70s6 kinase ($p70^{s6k}$). $p70^{s6k}$ in turn phosphorylates the 40s ribosomal protein S6, which favors translation of mRNAs that encode ribosomal proteins and elongation factors. Another target of mTOR is a low-molecular-weight repressor of translation initiation termed phosphorylated heat- and acid-stable protein regulated by insulin (PHAS-I). Phosphorylation of PHAS-I results in its dissociation from eukaryotic initiation factor (eIF)-4E and increases eIF-4E-dependent translation initiation.

Rapamycin has been reported to inhibit cell cycle progression in a variety of cell types, including human T cells and B cells. In addition, rapamycin has in vitro and in vivo activity against a broad range of human tumor cell lines and is considered to represent a promising new class of cytostatic anticancer agents.

SUMMARY OF THE INVENTION

In one aspect, the present invention provides rapamycin polymorph Form II. Advantageously, this polymorph has increased compressibility as compared to Form I, providing mechanical advantages for formulation and other processing.

In another aspect, the present invention provides a process for preparing rapamycin polymorph Form II.

In a further aspect, the present invention provides pharmaceutical compositions containing rapamycin polymorph Form II.

In yet another aspect, the present invention provides kits containing rapamycin polymorph Form II.

In still a further aspect, the present invention provides methods of preparing pharmaceutical compositions containing rapamycin polymorph Form II.

Other aspects and advantages of the present invention are described further in the following detailed description of the preferred embodiments thereof.

DETAILED DESCRIPTION OF THE INVENTION

The present invention provides rapamycin polymorph Form II and provides a new process to make Form I from Form II by removing the solvate. Rapamycin polymorph Form II was isolated and characterized by X-ray diffraction (XRD), differential scanning calorimetry (DSC), and thermogravimetric analysis (TGA). Rapamycin polymorph Form II has a lower melting point than rapamycin and is more readily compressible than Form I, forming a smooth surface upon compression. The distinguishable property of Form I from this new process is that it can be converted to Form II totally in the environment of t-butyl methyl ether vapor.

The following will provide further advantages of rapamycin polymorph Form II and methods of obtaining and using the same.

I. Definitions

Figure 1:
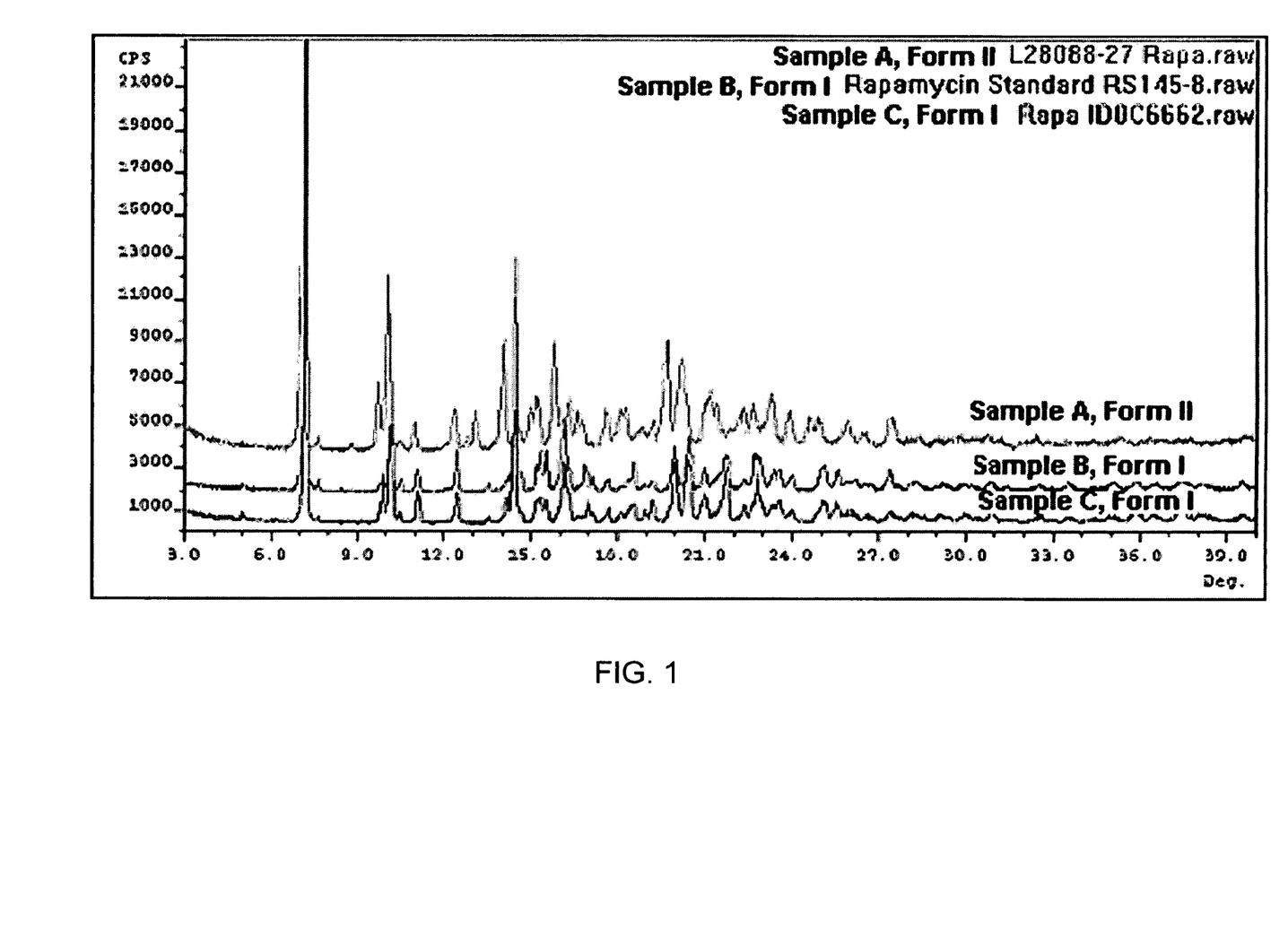
FIG. 1 provides X-ray diffraction (XRD) patterns of rapamycin polymorph Form II. The XRD pattern of rapamycin polymorph Form II is the top set of peaks, a standard is provided in the middle and the XRD pattern of rapamycin is the bottom set of peaks.

As used herein, the term "rapamycin" refers to the rapamycin form currently available to those in the art, which is identified by characteristic and readily available or obtainable high performance liquid chromatography retention times, X-ray crystal structure, powder XRD pattern, and DSC thermogram. The powder XRD pattern of rapamycin is readily available to those of skill in the art and contains several peaks of varying intensity at 2θ of about 7.2°, 9.9°, 10.2°, 11.1°, 12.5°, 14.5°, 15.3°, 15.5°, 16.2°, 20.0°, 20.4°, and 21.8°. See the bottom XRD pattern for rapamycin in FIG. 1. The X-ray crystal structure of rapamycin has an orthorhombic space group $P2_12_12_1$ with a=34.85(2)Å, b=13.08(1) Å, c=12.25(1) Å (D. C. Neil Swindwells et al *Can. J. Chem.* 56, 2491, 1978, which is hereby incorporated by reference). The DSC thermogram of rapamycin is characterized by a sharp melting endotherm at about 194° C.

As used herein, the term "polymorph" refers to a compound (e.g., rapamycin) which, when present as a solid, exists as different forms. Desirably, the rapamycin polymorph includes solid forms of a compound such as crystals, microcrystals, foams, and powders, among others. Preferably, the rapamycin polymorphs of the present invention are crystalline. Polymorphs typically differ in their physical properties due to the order of the molecules in the lattice of the polymorph. In addition, the physical properties of the polymorph can differ due to the presence of solvates or other molecules incorporated into the lattice of the polymorph. Typically, polymorphs are readily distinguished using techniques such as melting point, rate of dissolution, Infrared and Raman spectroscopy, and X-ray diffraction such as crystal and powder techniques.

The term "amorphous" as used herein refers to a compound having no definite crystal structure or form. In the present application, the term amorphous refers to amorphous rapamycin that can be present in the amorphous form as a solid or in a solution.

The term "precipitation" or "precipitating" is meant to describe a process by which a solid form of a compound is precipitated from a solution containing dissolved compound. As used herein, precipitation is meant to describe precipitating rapamycin polymorph Form II from a solution of rapamycin, preferably in t-butyl methyl ether.

The term "room temperature" is meant to describe a temperature of about 23 to about 25° C. However, one of skill in the art would readily understand that the specific room temperature can vary depending upon the conditions utilized during the formation of rapamycin polymorph Form II and environmental conditions.

II. Methods of Preparing Rapamycin Polymorph Form II

In one aspect, the present invention provides methods for preparing rapamycin polymorph Form II. Preferably, rapamycin polymorph Form II is prepared from amorphous rapamycin. The particular process utilized to produce amorphous rapamycin from rapamycin is however not a limitation on the present invention.

Rapamycin is combined with an initial solvent that is capable of dissolving rapamycin. Typically, the initial solvent is acetone. The initial solvent is then removed using reduced pressures of less than about 1 atmosphere (atm), typically by use of a rotavap and at elevated temperatures of about 40° C. to 50° C. After removal of the initial solvent, solid rapamycin is re-formed, preferably in an amorphous form. Lower or higher temperatures can be utilized to remove the initial solvent, but the use thereof should not be considered a limitation of the present invention. Typically, the solid rapamycin formed after initial solvent removal is a foam. However, rapamycin obtained after initial solvent removal can be a powder or an oil.

After removal of the initial solvent, the amorphous rapamycin is dissolved in a second dissolving solvent. In one embodiment, the second dissolving solvent is an ether, preferably t-butyl methyl ether (TBME). The ether can be dehydrated or can contain water. Preferably, rapamycin is dissolved in the second dissolving solvent at elevated temperatures of about 45° C. However, one of skill in the art would readily be able to utilize temperatures below or above 45° C. to dissolve rapamycin in the second dissolving solvent.

After addition of rapamycin to the second dissolving solvent, the solution is mixed for at least about 1 minute. Typically, rapamycin is initially combined with the second dissolving solvent at the elevated temperatures noted above. However, lower temperatures can be utilized to promote formation of rapamycin polymorph Form II and can readily be selected by one of skill in the art. Typically, the temperature is lowered to and maintained at a temperature of about room temperature. The solution is generally maintained at about room temperature for about 6 to about 12 hours. One of skill in the art would readily be able to determine the type of mixing employed, the period of time, and temperatures required to dissolve amorphous rapamycin in the dissolving solvent. Preferably, rapamycin is dissolved in TBME at about 45° C. and then maintained at room temperature for about 6 to about 8 hours.

After dissolution of rapamycin and maintenance in the second dissolving solvent, solid samples of rapamycin polymorph Form II are formed in the solution via precipitation. Typically, rapamycin polymorph Form II is precipitated as white crystals. However, rapamycin polymorph Form II can precipitate as a fine or coarse powder. Rapamycin polymorph Form II can be isolated using techniques known to those of skill in the art and include filtration, decanting, centrifugation and chromatography, among others. Typically, filtration is utilized to isolate the precipitated rapamycin polymorph Form II sample. The residual dissolving solvent obtained after filtration can optionally be concentrated and/or cooled to temperatures lower than about room temperature to promote the precipitation of additional rapamycin polymorph Form II.

Once isolated, residual solvent can be removed by air-drying or under an inert atmosphere such as nitrogen. Typically, any residual solvent is removed over a period of time of at least 0.5 hours and preferably, about 0.5 to 3 hours.

In one embodiment, the present invention provides a process for preparing rapamycin polymorph Form II including dissolving rapamycin in acetone; removing the acetone to form a foam; dissolving the foam in t-butyl methyl ether; and collecting rapamycin polymorph Form II.

III. Characterization of Rapamycin Polymorph Form II

Characterization of rapamycin polymorph Form II and distinguishing the same from rapamycin is accomplished using techniques known to those of skill in the art. Specifically, verification that rapamycin polymorph Form II is present after precipitation can be performed using techniques including melting point, infrared spectroscopy (IR), nuclear magnetic resonance spectroscopy (NMR), mass spectral analysis (MS), combustion analysis, Raman spectroscopy, elemental analysis, and chromatography including high performance liquid chromatography. Other techniques including differential scanning calorimetry (DSC) and X-ray diffraction (XRD) are also useful in distinguishing polymorphs, and specifically, rapamycin from rapamycin polymorph Form II.

(A) Identification Using Spectroscopy

HPLC can be utilized to verify that the product obtained as noted above is rapamycin polymorph Form II. Preferably, the rapamycin polymorph is analyzed using HPLC-Ultra Violet (UV) or HPLC-Mass Spectral (MS) Spectroscopy using the techniques described in French et al., *Clinical Chemistry*, 47(7): 1316 (2001) and Holt et al., *Clinical Chemistry*, 46(8): 1179 (2000), which are hereby incorporated by reference.

Desirably, the HPLC chromatograph of rapamycin polymorph Form II is identical to the HPLC chromatograph of rapamycin using the conditions described in French and Holt noted above. The HPLC chromatograph of rapamycin polymorph Form II may contain additional peaks that correspond to impurities that can be readily identified by one of skill in the art. However, one of skill in the art would readily understand that the presence of the impurities does not interfere with identification and characterization of rapamycin polymorph Form II.

A variety of HPLC conditions useful for obtaining a HPLC chromatograph can readily be determined by one of skill in the art, and should not be considered a limitation on the present invention. These HPLC conditions include variations in the column temperature, flow rate, detection wavelength, column type, column size, and mobile phase, among others. In one embodiment, the HPLC-MS conditions include the conditions set forth in Holt noted above. For example, the conditions include a 15 centimeter (cm)×4.6 mm Supelcosil™ LC-18-DB column containing 5 micron (µ) ODS particles, a temperature of about 50° C., and a flow rate of about 1.0 milliliter (mL)/minute. A variety of mobile phases can be utilized to obtain an HPLC-UV chromatograph of rapamycin polymorph Form II. In one embodiment, the mobile phase is a methanol:water (for example, 80:20 by volume) solution optionally supplemented with an ammonium acetate solution or other solvent such as acetonitrile and/or dioxane, among others.

By using the HPLC-MS conditions as noted above, the HPLC chromatograph having a retention time of about 6 minutes should be obtained for rapamycin polymorph Form II. The HPLC-MS chromatograph of rapamycin polymorph Form II can then be compared to the HPLC-MS of rapamycin using the same HPLC-MS conditions. In the present invention, the retention time for rapamycin polymorph Form II should be identical to the retention time of about 6 minutes for rapamycin.

Typically, XRD and DSC techniques are utilized as further confirmation to verify that rapamycin polymorph Form II is present.

(B) Identification Using X-ray Diffraction

XRD techniques are utilized to distinguish rapamycin polymorph Form II from rapamycin. One of skill in the art would readily be able to determine the conditions required to obtain an XRD pattern of rapamycin polymorph Form II. A variety of XRD instruments are available and include the Scintag™ X-2 Advanced Diffraction System instrument using the Diffraction Management Software NT program, among others.

The powder XRD pattern of rapamycin polymorph Form II described herein was therefore obtained using X-ray crystallographic techniques known to those of skill in the art. In one embodiment, the XRD pattern of rapamycin polymorph Form II includes multiple peaks that differ from the XRD peaks obtained for rapamycin. In another embodiment, the XRD pattern of rapamycin polymorph Form II contains one large peak and several smaller peaks. In a further embodiment, the XRD pattern of rapamycin polymorph Form II contains peaks at 2θ of about 7°, 9.7°, 10.1°, 11.0°, 12.4°, 13.1°, 14.1°, 14.6°, 15.0°, 15.2°, 15.8°, 16.3°, 16.6°, 17.6°, 18.1°, 18.3°, 19.7°, 20.2°, and 21.2°.

Other peaks can also be present in the XRD pattern of rapamycin polymorph Form II and correspond to impurities in the sample. The other peaks typically correspond to minor amounts of rapamycin and/or free t-butyl methyl ether not incorporated into the matrix of rapamycin polymorph Form II.

In addition to characterizing rapamycin polymorph Form II, XRD can be used to monitor the formation of rapamycin polymorph Form II. Typically, samples are obtained at various stages during dissolution in the second dissolving solvent and during precipitation of rapamycin polymorph Form II and the XRD patterns obtained therefrom.

(C) Identification Using Differential Scanning Calorimetry

Differential scanning calorimetry (DSC) techniques can also be utilized to distinguish rapamycin polymorph Form II from rapamycin. One of skill in the art would readily be able to determine the conditions necessary to obtain a DSC thermogram of rapamycin polymorph Form II. A variety of differential scanning calorimeters are available by those of skill in the art and include the Pyris™ 1 DSC instrument, using temperatures of about 25° C. to about 220° C. and temperature increases at various rates including 5° C./min., 10° C./min., and 30° C./min., among other instruments and conditions.

Figure 2:
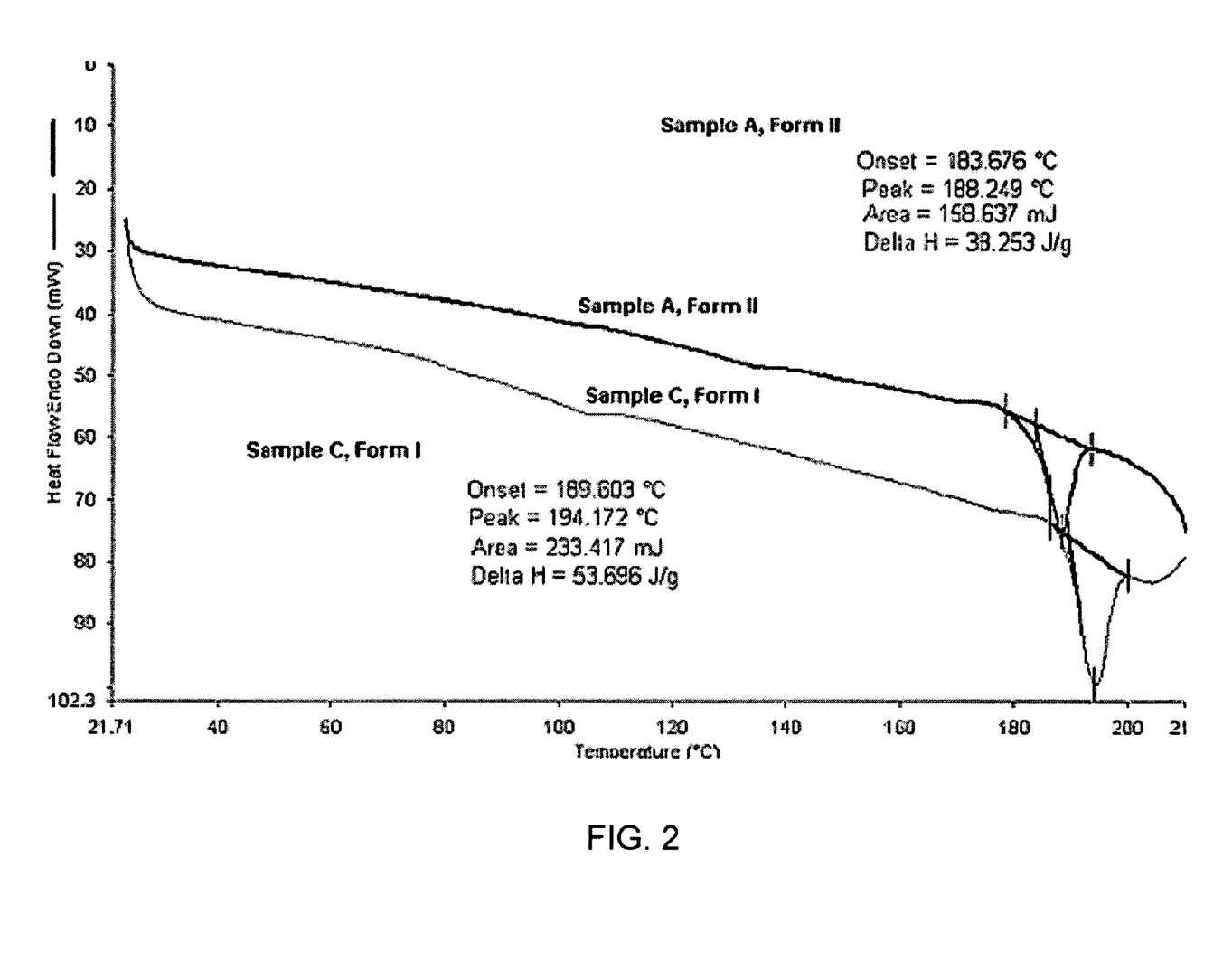
FIG. 2 provides differential scanning calorimetry (DSC) thermograms for rapamycin and rapamycin polymorph Form II. The DSC thermogram of rapamycin is located below the DSC thermogram of rapamycin polymorph Form II.

The DSC thermogram of rapamycin polymorph Form II prepared according to the present invention lacks the endotherm peak of about 194° C. that is present in the XRD pattern for rapamycin. The DSC thermogram instead contains an endotherm peak of about 188°. See, FIG. 2. The DSC thermogram of rapamycin polymorph Form II can also include degradation endotherms. Without wishing to be bound by theory, an endotherm corresponding to residual t-butyl methyl ether can also be present.

In one embodiment, rapamycin polymorph Form II can therefore be prepared having a DSC thermogram containing an endotherm peak at about 188° C. and lacking an endotherm peak of about 194° C.

(D) Identification Using Thermogravimetric Analysis (TGA)

TGA can also be utilized to determine the presence of solvate molecules, such as TBME molecules, in the sample of rapamycin polymorph Form II. In the present invention, the ratio of the rapamycin molecule to the trapped solvent molecules in the rapamycin polymorph Form II is about 2:1 and the solvent molecules therefore include about 4% of the solid sample. One of skill in the art would readily be able to determine the instruments and conditions utilized during TGA.

IV. Conversion of Rapamycin Polymorph Form II to Other Rapamycin Forms

Rapamycin polymorph Form II can be converted to the corresponding esters, carbamates, sulfates, ethers, oximes, carbonates, the like using techniques known to those of skill in the art. For example, rapamycin polymorph Form II can be converted to rapamycin 42-ester with 3-hydroxy-2-(hydroxymethyl)-2-methylpropionic acid (CCI-779).

Rapamycin polymorph Form II can also be desolvated to form special rapamycin Form I, or a mixture of rapamycin Form I and rapamycin polymorph Form II. Typically, Form II is converted to Form I, or a mixture of Form II with Form I, by heating solid Form II at temperatures greater than about 60° C. Alternatively, Form II can be converted to Form I, or a mixture of Form II with Form I, by use of vacuums. Vacuums having pressures less than about 1 atmosphere (atm) can be utilized in the present invention to desolvate rapamycin polymorph Form II. Preferably, vacuums obtained by the use of a speedvac are desirable. Such vacuums can be maintained for short or extended periods of time. One of skill in the art would readily be able to determine the amount of time required to desolvate rapamycin polymorph Form II. In one embodiment, the vacuum is maintained for at least about 8 hours. In another embodiment, the vacuum is maintained for at least about 2 days. In a further embodiment, the vacuum is maintained for about 2 days to about 7 days.

Without wishing to be bound by theory, the inventors have discovered that rapamycin polymorph Form II is a solvate, containing about 4% solvent. The solvent can be removed to produce a special rapamycin polymorph Form I which has an identical X-ray diffraction pattern to rapamycin Form I but very slightly different physical properties as detailed below. Thus, the invention provides rapamycin polymorph Form I prepared by desolvating rapamycin polymorph Form II. The inventors have also discovered that the special Form I can be converted to Form II totally in the environment of t-butyl methyl ether vapor. This contrasts with regular rapamycin Form I produced by prior art that does not completely form rapamycin polymorph Form II when exposed to solvent.

Desirably, rapamycin polymorph Form II is converted to rapamycin Form I by heating Form II to temperatures greater than about 100° C. under reduced pressures. The inventors have also discovered that rapamycin Form I can be resolvated in the vapor of the dissolving solvent, preferably TBME vapor, to form rapamycin polymorph Form II.

V. Compositions Containing Rapamycin Polymorph Form II

Compositions containing rapamycin polymorph Form II can also be prepared according to the present invention. Such compositions are prepared by combining rapamycin polymorph Form II and a pharmaceutically acceptable carrier.

In one embodiment, the invention provides a composition or mixture of rapamycin polymorph Form II and/or special rapamycin polymorph Form I along with one or more other crystalline, polymorphic, solvate, amorphous, or other forms of rapamycin. For example, such a composition may comprise rapamycin polymorph Form II along with one or more other forms of rapamycin, such rapamycin and/or rapamycin polymorph Form I. In another example, such a composition may comprise rapamycin polymorph Form I along with one or more other forms of rapamycin, such as rapamycin and/or rapamycin polymorph Form II. More specifically, the composition may comprise from 0.5% to 100% by weight of rapamycin polymorph Form II or rapamycin polymorph Form I, or any amount in between. For example, the composition may comprise less than 1%, 2%, 5%, 10%, 20%, 30%, 40% or 50% by weight of rapamycin polymorph Form II or rapamycin polymorph Form I based on the total amount of the composition. Alternatively, the composition may comprise at least 50%, 60%, 70%, 80%, 90%, 95%, 97%, 98%, 99%, 99.5% or 99.9% by weight of rapamycin polymorph Form II and/or rapamycin polymorph Form I based on the total amount of rapamycin in the composition.

In a further embodiment, prior to administration, rapamycin polymorph Form II or rapamycin polymorph Form I may be formulated as a pharmaceutical composition that contains an effective dosage amount of rapamycin polymorph Form II and/or Form I in combination with one (or more) pharmaceutically acceptable carrier(s).

In still another embodiment, the pharmaceutical composition comprises an effective dosage of a rapamycin composition that comprises at least a certain percentage of rapamycin polymorph Form II or rapamycin polymorph Form I (based on the total amount of rapamycin present in the composition, i.e., the total amount of rapamycin forms being 100%). In other words, at least a certain percentage of rapamycin present within the pharmaceutical composition exists as rapamycin polymorph Form II or rapamycin polymorph Form I, with the remainder of rapamycin being in a different form, including (but not limited to) rapamycin, rapamycin polymorph Form II, rapamycin polymorph Form I, or any other crystalline, polymorphic, solvate or amorphous form(s).

The compositions described herein containing rapamycin polymorph Form II can be formulated in any form suitable for the desired route of delivery using a pharmaceutically effective amount of rapamycin polymorph Form II. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

The oral dosage tablet composition of this invention can also be used to make oral dosage tablets containing derivatives of rapamycin polymorph Form II, including, but not limited to, esters, carbamates, sulfates, ethers, oximes, carbonates, the like which are known to those of skill in the art.

The increased compressibility of Form II as compared to Form II is anticipated to be particularly advantageous for tabletting and providing a smooth surface area.

A pharmaceutically effective amount of rapamycin polymorph Form II can vary depending on the specific compound(s), mode of delivery, severity of the condition being treated, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

Rapamycin polymorph Form II can be combined with one or more pharmaceutically acceptable carriers or excipients including, without limitation, solid and liquid carriers that are compatible with the compositions of the present invention. Such carriers include adjuvants, syrups, elixirs, diluents, binders, surfactants, water soluble polymers, lubricants, surfactants, granulating agents, disintegrating agents, emollients, metal chelators, pH adjustors, surfactants, fillers, disintegrants, suspending and stabilizing agents, and combinations thereof, among others. In one embodiment, rapamycin polymorph Form II is combined with metal chelators, pH adjustors, surfactants, fillers, disintegrants, lubricants, and binders.

Adjuvants can include, without limitation, flavoring agents, coloring agents, preservatives, and supplemental antioxidants, which can include vitamin E, citric acid, ascorbic acid, butylated hydroxytoluene (BHT), butylated hydroxyanisole (BHA), d,l-α-tocopherol, monothioglycerol, and propyl gallate. Typical concentrations of the antioxidants utilized in the oral formulations used in this invention will be used in concentrations ranging from 0.0005 to 0.5% w/v.

Lubricants can include magnesium stearate, light anhydrous silicic acid, talc, stearic acid, sodium lauryl sulfate, and sodium stearyl furamate, among others. In one embodiment, the lubricant is magnesium stearate, stearic acid, or sodium stearyl furamate. In another embodiment, the lubricant is magnesium stearate.

Granulating agents can include, without limitation, silicon dioxide, microcrystalline cellulose, starch, calcium carbonate, pectin, and crospovidone, polyplasdone, among others.

Binders, fillers, and disintegrants can include starch, mannitol, calcium phosphate, sugars such as sucrose, kaolin, lactose, and dextrose, croscarmellose sodium, magnesium stearate, gum acacia and arabic, cholesterol, tragacanth, stearic acid, gelatin, casein, lecithin (phosphatides), carboxymethylcellulose, carboxymethylcellulose calcium, carboxymethylcellulose sodium, methylcellulose, hydroxyethylcellulose, hydroxymethylcellulose, hydroxypropylcellulose, hydroxypropylmethycellulose phthalate, noncrystalline cellulose, microcrystalline cellulose, cetostearyl alcohol, cetyl alcohol, cetyl esters wax, dextrates, dextrin, glyceryl monooleate, glyceryl monostearate, glyceryl palmitostearate, polyoxyethylene alkyl ethers, polyethylene glycols, polyoxyethylene castor oil derivatives, polyoxyethylene stearates, polyvinyl alcohol, substituted sodium bicarbonate, calcium citrate, sodium starch glycolate, pregelatinized starch, crospovidone, polypropylpyrrolidone, polyvinylpyrrolidone (povidone, PVP), cholesterol, stearic acid, gelatin, casein, lecithin (phosphatides), and the like may also be incorporated into the oral formulation.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include nonionic and anionic agents including polysorbates such as polysorbate 20 and 80, sorbitan esters, poloxamers such as poloxamer 188, sodium lauryl sulfate, sodium dodecyl sulfate, benzalkonium chloride, calcium stearate, cetostearyl alcohol, cetomacrogol emulsifying wax, colloidal silicon dioxide, phosphates, magnesium aluminum silicate, triethanolamine, or salts of bile acids (taurocholate, glycocholate, cholate, deoxycholate, etc.) that may be combined with lecithin. The surfactants can also include ethoxylated vegetable oils, such as Cremophor EL or pegylated castor oil [e.g., such as PEG-35 castor oil which is sold, e.g., under the name Cremophor EL, BASF], vitamin E tocopherol propylene glycol succinate (Vitamin E TGPS), polyoxyethylene-polyoxypropylene block copolymers, and poloxamers. It is expected that the surfactant can contain 0.5 to 100% w/v of the composition, 0.5% to 10% w/v, 5 to 80% w/v, 10 to 75% w/v, 15 to 60% w/v, and preferably, at least 5% w/v or at least 10% w/v, of the composition.

Metal chelators can include physiologically acceptable chelating agents including edetic acid, malic acid, fumaric acid, ethylene diamine tetra acetic acid (EDTA), or amino acids such as glycine that are capable of enhancing the stability of rapamycin polymorph Form II. In one embodiment, the metal chelator is edetic acid.

pH adjusters can also be utilized to adjust the pH of a solution containing rapamycin to about 4 to about 6. In one embodiment, the pH of a solution containing rapamycin is adjusted to a pH of about 4.6. pH adjustors can include physiologically acceptable agents including citric acid, ascorbic acid, fumaric acid, malic acid, or dilute hydrochloric acid, and salts thereof. In one embodiment, the pH adjuster is citric acid.

Water-soluble polymers include, but are not limited to, polyvinylpyrrolidone (PVP), hydroxypropylmethylcellulose (HPMC), polyethylene glycol (PEG), and cyclodextrin or mixtures thereof. It is preferred that the water-soluble polymer is PVP, and having a molecular weight of between 2.5 and 60 kilodaltons. Any given oral formulation useful in the invention may contain multiple ingredients of each class of component. For example, an oral formulation containing an antioxidant may contain one or more antioxidants as the antioxidant component.

Suspending or stabilizing agents can include, but are not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar.

Diluents can include water, ethanol, polyethylene glycol 300, polyethylene 400, polyethylene 600, polyethylene 1000, or blends containing one or more of these polyethylene glycols, propylene glycol and other pharmaceutically acceptable cosolvents or agents to adjust solution osmolarity such as sodium chloride, lactose, mannitol or other parenterally acceptable sugars, polyols and electrolytes.

In one embodiment, compositions containing rapamycin polymorph Form II are delivered orally by tablet, caplet or capsule, microcapsules, dispersible powder, granule, suspension, syrup, elixir, and aerosol. Desirably, when compositions containing rapamycin polymorph Form II are delivered orally, delivery is by tablets and hard- or liquid-filled capsules.

Non-alcoholic solvents can include dimethylacetamide, dimethylsulfoxide or acetonitrile, or mixtures thereof, among others.

Alcoholic solvents can include one or more alcohols as the alcoholic solvent component of the formulation.

Particularly suitable oral formulations for rapamycin polymorph Form II include the same formulations utilized with CCI-779 and described in US Patent Publication No. US-20040077677 and International Patent Publication No. WO 04/026280 (Application No. PCT/US03/29228), which are hereby incorporated by reference. Such oral formulations contain a granulation prepared using a wet granulation process. The granulation can contain rapamycin polymorph Form II, a water-soluble polymer, a pH modifying agent, a surfactant, and an antioxidant. In one embodiment, the formulation contains from 0.1 to 30%, from 0.5 to 25%, from 1 to 20%, from 5 to 15%, or from 7 to 12% (wt/wt) rapamycin polymorph Form II; from 0.5 to 50%, from 1 to 40%, from 5 to 35%, from 10 to 25%, or from 15 to 20% (wt/wt) water soluble polymer; from 0.5 to 10%, 1 to 8%, or 3 to 5% (wt/wt) surfactant; and from 0.001% to 1%, 0.01% to 1%, or 0.1% to 0.5% (wt/wt) antioxidant. However, other embodiments may contain more, or less, of these components.

In another embodiment, the compositions containing rapamycin polymorph Form II can be delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile and stable under conditions of manufacture and storage, and free of the contaminating action of microorganisms such as bacteria and fungi. Under ordinary conditions of storage and use, these preparations contain a preservative to prevent the growth of microorganisms.

A parenteral formulation useful in the invention can be prepared as a single solution, or preferably can be prepared as a cosolvent concentrate containing rapamycin polymorph Form II, an alcoholic solvent, and an antioxidant, which is subsequently combined with a diluent that contains a diluent solvent and suitable surfactant.

When prepared as a single solution or dispersion, rapamycin polymorph Form II is combined with a diluent. In one embodiment, rapamycin polymorph Form II is combined with water, optionally mixed with a surfactant such as hydroxy-propylcellulose. Dispersions can be prepared in glycerol, liquid polyethylene glycols and mixtures thereof in oils.

Particularly suitable injectable formulations for rapamycin polymorph Form II include those injectable formulations utilized for CCI-779 in US Patent Publication No. 20040167152-A1 (application Ser. No. 10/626,943); International Patent Publication No. WO 03/23267 (Application No. PCT/US03/223276); International Patent Publication No. WO 2004/011000; and US Patent Publication No. 20040167152-1A (application Ser. No. 10/626,943), which are hereby incorporated by reference. Any given formulation useful in this invention may contain multiple ingredients of each class of component. In one embodiment, a parenterally acceptable solvent can include a non-alcoholic solvent, an alcoholic solvent, or mixtures thereof. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These solvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v of ethanol in the mixture is preferred.

The stability of rapamycin polymorph Form II in the parenterally acceptable alcoholic cosolvents can be enhanced by addition of an antioxidant to the formulation. Generally, the parenteral formulations useful in this embodiment of the invention will contain an antioxidant component (s) in a concentration ranging from 0.001% to 1% w/v, or 0.01% to 0.5% w/v, of the cosolvent concentrate, although lower or higher concentrations may be desired. Of the antioxidants, d,l-α-tocopherol is particularly desirable and is used at a concentration of 0.01 to 0.1% w/v with a preferred concentration of 0.075% w/v of the cosolvent concentrate.

Advantageously, in certain embodiments of the parenteral formulations useful in the invention, precipitation of rapamycin polymorph Form II upon dilution with aqueous infusion solutions or blood is prevented through the use of a surfactant contained in the diluent solution. One particularly desirable surfactant is polysorbate 20 or polysorbate 80, as noted below. However, one of skill in the art may readily select other suitable surfactants.

Prior to use, the cosolvent concentrate is mixed with a diluent comprising a diluent solvent, and a surfactant. When rapamycin polymorph Form II is prepared as a cosolvent concentrate according to this invention, the concentrate can contain concentrations of rapamycin polymorph Form II from 0.05 mg/mL, from 2.5 mg/mL, from 5 mg/mL, from 10 mg/mL or from 25 mg/mL up to approximately 50 mg/ml. The concentrate can be mixed with the diluent up to approximately 1 part concentrate to 1 part diluent, to give parenteral formulations having concentrations of rapamycin polymorph Form II from 1 mg/mL, from 5 mg/mL, from 10 mg/mL, from 20 mg/mL, up to approximately 25 mg/ml. For example the concentration of rapamycin polymorph Form II in the parenteral formulation may be from about 2.5 to 10 mg/mL. This invention also covers the use of formulations having lesser concentrations of rapamycin polymorph Form II in the cosolvent concentrate, and formulations in which one part of the concentrate is mixed with greater than 1 part of the diluent, e.g., concentrate: diluent in a ratio of about 1:1.5, 1:2, 1:3, 1:4, 1:5, or 1:9 v/v and so on, to rapamycin polymorph Form II parenteral formulations having a rapamycin polymorph Form II concentration down to the lowest levels of detection.

For the purposes of this disclosure, transdermal administrations are understood to include all administrations across the surface of the body and the inner linings of bodily passages including epithelial and mucosal tissues. Such administrations may be carried out using rapamycin polymorph Form II, or pharmaceutically acceptable salts thereof, in lotions, creams, foams, patches, suspensions, solutions, and suppositories (rectal and vaginal).

Transdermal administration may be accomplished through the use of a transdermal patch containing rapamycin polymorph Form II and a carrier that is inert to rapamycin polymorph Form II, is non-toxic to the skin, and allows delivery of the agent for systemic absorption into the blood stream via the skin. The carrier may take any number of forms such as creams and ointments, pastes, gels, and occlusive devices. The creams and ointments may be viscous liquids or semisolid emulsions of either the oil-in-water or water-in-oil type. Pastes comprised of absorptive powders dispersed in petroleum or hydrophilic petroleum containing rapamycin polymorph Form II may also be suitable. A variety of occlusive devices may be used to release rapamycin polymorph Form II into the blood stream such as a semi-permeable membrane covering a reservoir containing rapamycin polymorph Form II with or without a carrier, or a matrix containing rapamycin polymorph Form II. Other occlusive devices are known in the literature.

In a further embodiment, compositions containing rapamycin polymorph Form II can be delivered rectally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

In another embodiment, compositions containing rapamycin polymorph Form II can be delivered vaginally in the form of a conventional suppository, cream, gel, ring, or coated intrauterine device (IUD).

In yet another embodiment, compositions containing rapamycin polymorph Form II can be delivered intranasally or intrabronchially in the form of an aerosol.

It is also contemplated that compositions of this invention containing rapamycin polymorph Form II can be co-administered with one or more other agents including anti-rejection chemotherapeutic agents.

The dosage requirements of rapamycin polymorph Form II can vary depending on the severity of the symptoms presented, the particular subject being treated, and the route of administration. One of skill in the art would readily be able to determine the amount of rapamycin polymorph Form II required. In one embodiment, about 2 to about 100 mg/day of rapamycin polymorph Form II is administered. In other embodiments, rapamycin polymorph Form II is administered at 5 mg/day to 75 mg/day, 10 mg/day to 50 mg/day, 15 mg/day to 35 mg/day, or about 20 mg/day to 25 mg/day.

Treatment can be initiated with dosages of rapamycin polymorph Form II smaller than those required to produce a desired effect and generally less than the optimum dose of rapamycin polymorph Form II. Thereafter, the dosage can be increased until the optimum effect under the circumstances is reached. Precise dosages will be determined by the administering physician based on experience with the individual subject being treated. In general, the compositions of this invention are most desirably administered at a concentration that will generally afford effective results without causing any harmful or deleterious side effects.

VI. Methods of Preparing Administrable Compositions Containing Rapamycin Polymorph Form II In one aspect, the present invention includes methods of preparing a pharmaceutical composition containing rapamycin polymorph Form II. The composition can be administered to a mammalian subject by several different routes as noted above and is desirably administered orally in solid or liquid form.

Oral formulations containing rapamycin polymorph Form II can contain any conventionally used oral forms, including tablets, capsules, buccal forms, troches, lozenges and oral liquids, suspensions or solutions. Such oral formulations containing rapamycin polymorph Form II can be formed by blending rapamycin polymorph Form II with one or more of the components described above. In one embodiment, the components of the composition are dry or wet blended. In another embodiment, the components are dry granulated. In a further embodiment, the components are suspended or dissolved in a liquid and added to a form suitable for administration to a mammalian subject. Oral formulations can also include standard delay or time-release formulations to alter the absorption of rapamycin polymorph Form II. The oral formulation may also consist of administering rapamycin polymorph Form II in water or a fruit juice, containing appropriate solubilizers or emulsifiers as needed.

Capsules may contain mixtures of rapamycin polymorph Form II with fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc, described above.

Useful tablet formulations may be made by conventional compression, wet granulation or dry granulation methods and utilize pharmaceutically acceptable diluents, binding agents, lubricants, disintegrants, surface modifying agents (including surfactants). It is preferred that the wet granulation be performed with a hydroalcoholic solvent system comprising water and an alcohol, with ethanol being the preferred alcoholic component.

Liquid forms containing rapamycin polymorph Form II can be formed by dissolving or suspending rapamycin polymorph Form II in a liquid suitable for administration to a mammalian subject.

In one embodiment, methods of preparing a pharmaceutical composition containing rapamycin polymorph Form II include combining rapamycin polymorph Form II, a metal chelator, a pH adjuster, a surfactant, a filler, a binder, a disintegrant, and a lubricant.

In another embodiment, methods of preparing a pharmaceutical composition containing rapamycin polymorph Form II include combining rapamycin polymorph Form II, a metal chelator, a pH adjuster, a surfactant, at least one filler, a binder, a disintegrant, and a lubricant.

The present invention also provides kits or packages of pharmaceutical compositions designed for use in the present invention. Kits of the present invention can include rapamycin polymorph Form II and a carrier suitable for administration to a mammalian subject as discussed above. The invention therefore includes a product containing (a) rapamycin polymorph Form II for use in treating a mammal. The invention also includes a pharmaceutical pack containing a course of treatment of a neoplasm for one individual mammal, wherein the pack contains (a) rapamycin polymorph Form II in unit dosage form.

Thus, rapamycin polymorph Form II of the invention can be formulated as a pharmaceutical composition and, optionally, assembled in the form of a kit, for use in treatment of a mammal.

VII. Methods of Using Rapamycin Polymorph Form II

Rapamycin polymorph Form II can be utilized in the treatment or prevention of a variety of conditions known to those of skill in the art that rapamycin is known to treat or prevent. Rapamycin polymorph Form II can therefore possess immunosuppressive, antirejection, antifungal, anti-inflammatory, antitumor, and antiproliferative activities.

Specifically, rapamycin polymorph Form II alone or in a composition or kit prepared as noted above can be used as an antineoplastic agent, and in particular, in treatment of solid tumors, including sarcomas and carcinomas; and more particularly against astrocytomas, prostate cancer, breast cancer, colon cancer, small cell lung cancer, and ovarian cancer; and adult T-cell leukemia/lymphoma. Rapamycin polymorph Form II containing compositions and kits are also useful treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus including systemic lupus erythematosus, rheumatoid arthritis, diabetes mellitus, myasthenia gravis, and multiple sclerosis; and diseases of inflammation such as psoriasis, dermatitis, eczema, seborrhea, bowel disorders including inflammatory bowel disease, pulmonary inflammation (including asthma, chronic obstructive pulmonary disease, emphysema, acute respiratory distress syndrome, bronchitis, and the like), cardiac inflammatory disease, and ocular inflammation such as ocular uveitis; anemia; adult T-cell leukemia/lymphoma; fungal infections; malignant carcinomas; hyperproliferative vascular diseases such as restenosis; graft vascular atherosclerosis; and cardiovascular disease, cerebral vascular disease, and peripheral vascular disease, such as coronary artery disease, cereberovascular disease, arteriosclerosis, atherosclerosis, nonatheromatous arteriosclerosis, vascular wall damage from cellular events leading toward immune mediated vascular damage, smooth muscle cell proliferation and intimal thickening following vascular injury, and inhibiting stroke or multiinfarct dementia.

Appropriate dosage regimens can be readily determined based upon the information provided herein.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of Rapamycin Polymorph Form II

Rapamycin (3 g) was dissolved in 20 mL acetone. The solvent was then removed at reduced pressures via the use of a rotavap at a temperature of about 40° C. to about 50° C. to obtain a foam. The rapamycin in dry foam was dissolved in t-butyl methyl ether (10 mL) at about 45° C. and then kept at room temperature overnight. The precipitated white crystals were collected by filtration and dried in open air or under an atmosphere of nitrogen gas for about 0.5 to about 3 hours. A total 2.5 g of rapamycin polymorph Form II was obtained.

Example 2

X-ray Diffraction Study of Rapamycin Polymorph Form II

The powder XRD analysis of rapamycin polymorph Form II was performed on a Scintag™ X-2 Advanced Diffraction System instrument (from Scintag Inc., USA). A normal focus copper x-ray tube at 1.8 kW scanning 1 degree/minute from 3.00 to 40.00 degree was utilized. The data were recorded by a computer with the Diffraction Management Software™ NT (DMSNT) program. The error was less than 0.1°.

The samples were ground to a fine powder and packed into a cavity style sample holder with a zero background plate. The peak positions characterized powder X-ray diffraction pattern of angle position (2θ) were reported and compared.

The powder XRD of rapamycin polymorph Form II contained peaks at 2θ at 7.0°, 9.7°, 10.1°, 11.0°, 12.4°, 13.1°, 14.1°, 14.6°, 15.0°, 15.2°, 15.8°, 16.3°, 16.6°, 17.6°, 18.1°, 18.3°, 19.7°, 20.2°, and 21.2°. See, FIG. 1.

Example 3

Differential Scanning Thermogram Study of Rapamycin Polymorph Form II

A differential scanning calorimeter (DSC) model Pyris™ 1 (Perkin Elmer) with Pyris™ manager software was used to analyze rapamycin polymorph Form II. About 4-5 mg of rapamycin polymorph Form II was added to aluminum pans and thereby sealed. The sample was heated from 25° C. to 220° C. at varying rates (5° C./min., 10° C./min and 30° C./min.). The nitrogen gas was purged at 50 mL/min.

The differential scanning calorimetry thermogram was obtained having an endotherm peak of about 188°. See, FIG. 2.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A rapamycin polymorph Form II which contains t-butyl methyl ether solvate molecules having the following characteristics:
   (a) X-ray diffraction peak pattern comprising peaks at 2θ of about 7.0°, 9.7°, 10.1°, 11.0°, 12.4°, 13.1°, 14.1°, 14.6°, 15.0°, 15.2°, 15.8°, 16.3°, 16.6°, 17.6°, 18.1°, 18.3°, 19.7°, 20.2°, and 21.2°; and
   (b) a differential scanning calorimetry thermogram having an endotherm peak of about 188°.

2. The rapamycin polymorph Form II according to claim 1, further having:
   (a) a differential scanning calorimetry thermogram lacking an endotherm peak of about 194°; and
   (b) an X-ray diffraction peak pattern lacking peaks at 2θ of 7.2°, 9.9°, 10.2°, 11.1°, 12.5°, 14.5°, 15.3°, 15.5°, 16.2°, 20.0°, 20.4°, and 21.8°.

3. The rapamycin polymorph Form II according to claim 1, wherein said solvate molecules comprise about 4% of said Form II as determined by thermogravimetric analysis TGA.

4. The rapamycin polymorph Form II according to claim 1, wherein the molecular ratio of said rapamycin to said solvate is about 2:1.

5. A rapamycin polymorph Form II obtained by recrystallizing rapamycin from t-butyl methyl ether.

6. A process for preparing rapamycin polymorph Form II comprising the steps of:
   dissolving amorphous rapamycin in t-butyl methyl ether and recrystallizing rapamycin to afford rapamycin form II.

7. The method according to claim 6, further comprising the steps of:
   dissolving rapamycin in an initial solvent and
   removing said initial solvent to provide amorphous raparnycin.

8. The method according to claim 7, wherein the rapamycin is dissolved in acetone at an elevated temperature.

9. The method according to claim 7 wherein the removing step is performed by rotavap to provide a foam.

10. The method according to claim 6, wherein the t-butyl methyl ether solution is maintained at an elevated temperature of about 40 to about 50° C.

11. The method according to claim 10, wherein said elevated temperature is about 45° C.

12. The method according to claim 11, further comprising the step of cooling said t-butyl methyl ether solution to about 23 to about 25° C.

13. The method according to claim 12, wherein said rapamycin polymorph Form II precipitates from said cooled t-butyl methyl ether solution.

14. The method according to claim 11, further comprising the step of drying said polymorph form II at a temperature less than about 23° C.

15. A process for preparing rapamycin polymorph Form I comprising desolvating rapamycin polymorph Form II.

16. The process according to claim 15, wherein said desolvating is performed using a vacuum.

17. The process according to claim 15, wherein said desolvating is performed at elevated temperature.

18. A solid pharmaceutical composition comprising rapamycin polymorph Form II according to claim 1 and a pharmaceutically acceptable carrier.

19. The pharmaceutical composition according to claim 18, wherein said carrier comprises one or more of a surfactant, at least one filler, a binder, a disintegrant, a metal chelator, a pH adjuster and a lubricant.

* * * * *